(12) United States Patent
Ahr et al.

(10) Patent No.: US 6,666,850 B1
(45) Date of Patent: *Dec. 23, 2003

(54) DISPOSABLE ABSORBENT ARTICLE WITH SELECTIVELY EXPANDABLE COMPONENTS

(75) Inventors: Nicholas A. Ahr, Cincinnati, OH (US); Gary D. Lavon, Cincinnati, OH (US); Brandon E. Wise, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/481,458

(22) Filed: Jan. 11, 2000

Related U.S. Application Data

(63) Continuation-in-part of application No. 08/422,676, filed on Apr. 13, 1995, now Pat. No. 6,180,847, which is a continuation of application No. 08/081,733, filed on Jun. 23, 1993, now abandoned.

(51) Int. Cl.$^7$ .......................... A61M 13/15; A61M 13/20
(52) U.S. Cl. .................. 604/385.12; 604/367; 2/DIG. 3
(58) Field of Search ............................ 604/369, 385.12, 604/385.19, 387, 358, 367, 352; 2/DIG. 3, DIG. 10; 128/118.1; 602/13; 606/202–204; 441/98–101

(56) References Cited

U.S. PATENT DOCUMENTS

| | | | |
|---|---|---|---|
| 3,512,528 A | 5/1970 | Whitehead et al. | |
| 3,921,232 A | 11/1975 | Whyte | ............................ 5/91 |
| 4,781,645 A | 11/1988 | Kato | ......................... 446/188 |
| 4,929,214 A | 5/1990 | Liebermann | ................ 446/221 |
| 5,306,266 A | 4/1994 | Freeland | |
| 5,330,459 A | 7/1994 | Lavon et al. | |
| 5,643,241 A | 7/1997 | Ahr et al. | |
| 5,876,393 A | 3/1999 | Ahr et al. | |
| 5,997,520 A | 12/1999 | Ahr et al. | |
| 6,180,847 B1 * | 1/2001 | Ahr et al. | ................... 604/367 |

FOREIGN PATENT DOCUMENTS

| | | |
|---|---|---|
| DE | 3517192 | 11/1986 |
| WO | 95/00089 | 1/1995 |

* cited by examiner

Primary Examiner—Karin Reichle
(74) Attorney, Agent, or Firm—Jay A. Krebs; David M. Weirich; Ken K. Patel

(57) ABSTRACT

A disposable absorbent article having an expandable component. The expandable component can be inflatable, and includes a gas evolving material and an activating material separated from the gas evolving material by a breakable barrier. The barrier is broken to combine the materials and inflate the component at the point of use of the disposable absorbent article. The inflatable component can include a spacer for maintaining a fecal void space in a disposable absorbent article.

10 Claims, 4 Drawing Sheets

DISPOSABLE ABSORBENT ARTICLE WITH SELECTIVELY EXPANDABLE COMPONENTS

This application is a continuation-in-part of application Ser. No. 08/422,676, filed on Apr. 13, 1995, now U.S. Pat. No. 6,180,847, which is a continuation of application Ser. No. 08/081,733, filed on Jun. 23, 1993, now abandoned.

FIELD OF THE INVENTION

The present invention is related to disposable absorbent articles having components that are selectively expandable by the user, such as by inflation.

BACKGROUND OF THE INVENTION

Disposable absorbent articles are well known in the art. Disposable absorbent articles are used to absorb and retain body exudates, such as urine, fecal material, menses, and the like. A particular desired feature of disposable absorbent articles is the capability to acquire and hold body exudates to eliminate, or at least minimize, leakage of body exudates from between the absorbent article and the wearer.

References in the prior art disclose a cavity or cutout in the absorbent core to receive fecal material. The fecal material passes through the topsheet and is received by the cavity or cutout in the absorbent core. These references suffer from the drawback that a cavity in the absorbent core decreases its absorbent capacity, and that the cavity is limited in volume to the size of the absorbent core. Examples of such teachings include U.S. Pat. No. 2,043,325 issued Jun. 9, 1936 to Jackson, Jr.; U.S. Pat. No. 4,731,065 issued Mar. 15, 1988 to Yamada; U.S. Pat. No. 4,834,737 issued May 30, 1989 to Khan; and U.S. Pat. No. 5,062,840 issued Nov. 5, 1991 to Holt, et al.

Other references teach adding a spacer to the disposable absorbent article. Such spacers can suffer from the drawback that they increase the thickness and bulkiness of the disposable absorbent article, and thereby increase shipping and storage costs. Such spacers may also be perceived by consumers to be uncomfortable because of their thickness and bulk prior to application of the diaper to the wearer. Examples of such references include U.S. Pat. No. 5,171,236, issued Dec. 15, 1992 to Dreier et al.; and U.S. Pat. No. 5,306,266, issued Apr. 26, 1994 to Freeland.

Still other references disclose absorbent articles having inflatable structures. French Patent Application 2,561,078 published Sep. 20, 1985 in the name of Lefebvre discloses a diaper having a structure which is inflatable by mouth. Such inflation can be awkward or inconvenient, especially in public places or when the diaper is already fastened to the wearer. Such an arrangement is also disadvantageous because of sanitary considerations, and because inflation may vary from consumer to consumer, resulting in over or under inflation of the structure and unpredictable product performance.

U.S. Pat. Nos. 3,881,491 and 3,921,232 issued to Whyte on May 6, 1975 and Nov. 25, 1975, respectively, disclose disposable absorbent articles having self inflating structures. The self inflating structures include a wall of semipermeable material and a gas evolving material. Upon exposing the outside of the semipermeable wall of the structure to an activator material, the activator material permeates the structure to interact with the gas evolving material, whereby the structure becomes inflated by evolved gas. The structure taught by Whyte primarily prevents core densification and suffers from the disadvantage that it requires an activator material from an external source (e.g., urine). The wearer may not urinate at the desired time, in the desired location, or in the desired amount to properly inflate the structure. Also, initial inflation of the Whyte structure can separate the gas evolving material from the semipermeable wall, thereby slowing or stopping further inflation of the structure.

Accordingly, it would be advantageous to provide an absorbent article having a component that is expandable. It would also be desirable to provide an absorbent article having a component that is inflatable at the point of use of the absorbent article by a wearer or by a person caring for the wearer, before or after the absorbent article is fastened to the wearer. Further, it would be desirable to provide an absorbent article comprising an inflatable component, a first material, and second activating material separated from the first material by a breakable barrier which can be broken to combine the first and second materials to inflate the component at the point of use of the absorbent article.

SUMMARY OF THE INVENTION

In order to solve the problems of the prior art, the present invention is directed to a disposable absorbent article having a topsheet, a backsheet, an absorbent core disposed intermediate the topsheet and backsheet, and an expandable component. The expandable component can expand from a first thickness to a second thickness. The disposable absorbent article further includes a system for controlling the expansion of the expandable component from the first thickness to the second thickness. The system includes a predetermined amount of a first material disposed on the article and a predetermined amount of a second material disposed on the article, wherein the second material is separated from the first material by a breakable barrier. The first and second materials are combinable by breaking the barrier to expand the expandable component. The system further includes an expansion control mechanism which is capable of controlling the rate of expansion of the expandable component.

BRIEF DESCRIPTION OF THE DRAWINGS

While the Specification concludes with claims particularly pointing out and distinctly claiming the present invention, the same will be better understood from the following description taken in conjunction with the associated drawings in which like reference numerals represent the same component.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and finer. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments such as sanitary napkins, tampons and the like.

Figure 1:
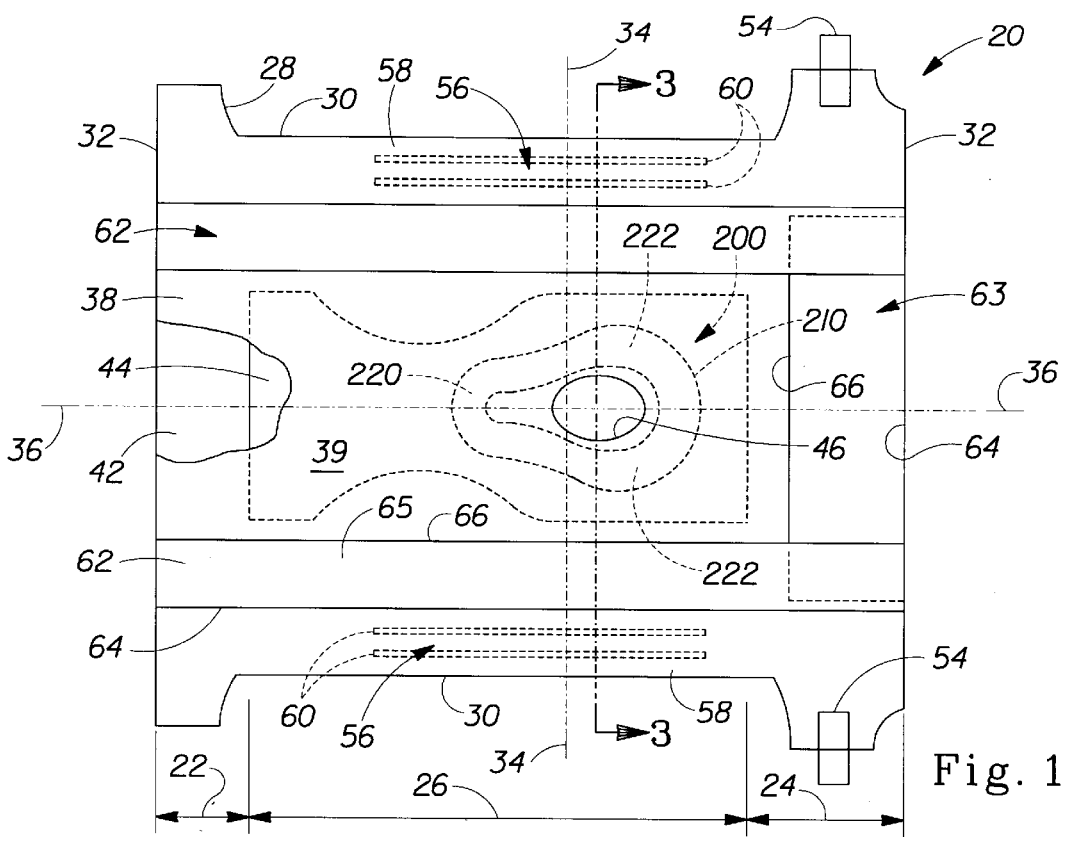
FIG. 1 is a top plan view of a disposable diaper embodiment of the present invention, the diaper shown partially cut-away and incorporating an inflatable keyhole-shaped spacer shown in phantom.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. The diaper 20 is shown in FIG. 1 to have a front waist region 22, a rear waist region 24, a crotch region 26, and a periphery 28 comprising longitudinal edges. 30 and front and rear end edges 32. The diaper 20 also has a lateral centerline 34 and a longitudinal centerline 36.

The front waist region 22 and the rear waist region 24 are those portions of the diaper 20 which, when worn, encircle the waist of the wearer and are generally the highest elevation of the diaper 20 when the wearer is in the standing position. The crotch region 26 is disposed between the front and rear waist regions 22, 24 and is that part of the diaper 20 which, when worn, is between the wearer's legs.

Figure 3:
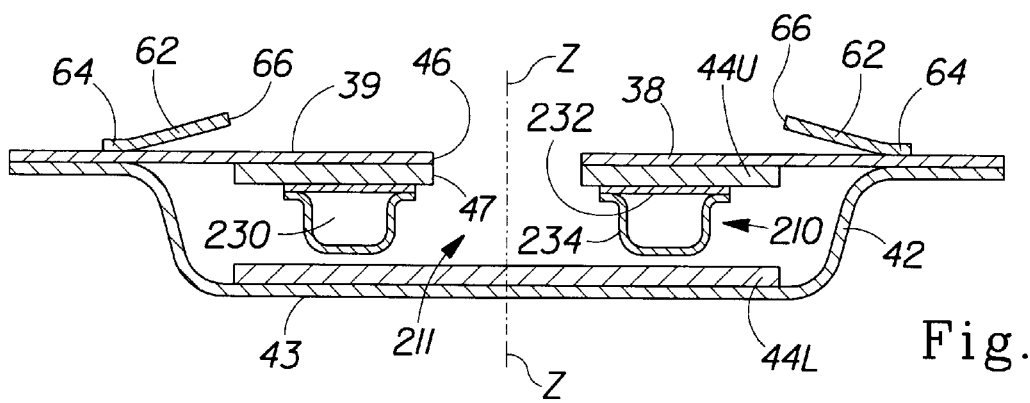
FIG. 3 is a cross-sectional view taken along line 3—3 of FIG. 1, with the spacer joined to an upper layer of the absorbent core.

As shown in FIG. 1, the diaper 20 preferably comprises a topsheet 38, a backsheet 42 joined with the topsheet 38, and an absorbent core 44 positioned between the topsheet 38 and the backsheet 42. The absorbent core 44 can comprise an upper layer joined to the topsheet 38 and a lower layer joined to the backsheet 42, as shown in FIG. 3. The diaper 20 has an inner surface 39 comprising that portion of the diaper 20 which is positioned adjacent to the wearer's body during use (i.e., the inner surface 39 generally is formed by at least a portion of the topsheet 38 and other components joined to the topsheet 38). The diaper also has an outer surface 43 comprising that portion of the diaper 20 which is positioned away from the wearer's body (i.e., the outer surface 43 generally is formed by at least a portion of the backsheet 42 and other components joined to the backsheet 42.

Referring to FIGS. 1, 3, 5, 6, and 7, the diaper 20 according to the present invention also comprises at least one expandable component 200 which is expandable from a first thickness T1 (FIG. 6) to a predetermined shape having a second thickness T2 (FIG. 7) substantially greater than the first thickness T1. The expandable component 200 can comprise a spacer 210 disposed intermediate the topsheet 38 and the backsheet 42 for maintaining a Z-direction fecal void space 211, as shown in FIG. 3. In at least one embodiment, the spacer 210 is preferably expandable by inflation.

The diaper 20 preferably also comprises a means or structure that the user can activate to expand the spacer 210 as desired. For example, in the embodiment shown in FIG. 5, the means for expanding the spacer 210 comprises a first material 300 disposed within the spacer 210, a second activating material 400, and a breakable barrier 490 separating the first and second materials 300, 400. The breakable barrier 490 can comprise a breakable packet 500 disposed in the spacer 210 and containing the second activating material 400. The wearer or diaperer breaks the packet 500, when desired, to combine the first and second materials 300, 400, and thereby expand the spacer 210. In one preferred embodiment the first material 300 comprises a gas evolving material which generates a gas upon combination with the second activating material 400 thereby inflating the spacer 210 from a first thickness T1 to a second thickness T2. (Other embodiments are described in more detail below.)

Referring to FIG. 1, the diaper 20 preferably also includes a pair of tape tab fasteners 54 positioned in the rear waist region 24 for fastening the diaper 20 to the wearer. The diaper 20. can also have gasket cuffs 56, each comprising a side flap 58 and one or more flap elastic members 60, as well as barrier leg cuffs 62, and a barrier waist cuff 63.

The diaper 20 may also include a waist elastic feature, such as an elasticized waist band. U.S. Pat. No. 3,848,594 issued Nov. 19, 1974 to Buell and U.S. Reissue Pat. No. B1 4,662,875 reissued May 5, 1987 to Hirotsu et al. are incorporated herein by reference to illustrate suitable tape tab fasteners 54. U.S. Pat. No. 3,860,003 issued Jan. 14, 1975 to Buell; U.S. Pat. No. 4,081,301 issued Mar. 28, 1978 to Buell; U.S. Pat. No. 4,695,278 issued Sep. 22, 1987 to Lawson; U.S. Pat. No. 4,808,177 issued Feb. 28, 1989 to Des Marais; and U.S. Pat. No. 4,938,755 issued Jul. 3, 1990 to Foreman are incorporated herein by reference to illustrate gasket cuffs 56, barrier leg cuffs 62, and a barrier waist cuff 63. U.S. Pat. No. 4,515,595 issued May 17, 1985 to Kievit; and U.S. Pat. No. 4,816,025 issued Mar. 28, 1989 to Foreman are incorporated herein by reference to illustrate an elasticized waistband for a diaper 20.

FIG. 1 shows a preferred embodiment of the diaper 20 in which the topsheet 38 and the backsheet 42 have length and width dimensions generally larger than those of the absorbent core 44. The topsheet 38 and the backsheet 42 preferably extend beyond the edges of the absorbent core 44 to thereby form the periphery 28 of the diaper 20. While the topsheet 38, the backsheet 42, and the absorbent core 44 may be assembled in a variety of well known configurations, preferred diaper configurations are described generally in U.S. Pat. No. 3,860,003 issued to Buell on Jan. 14, 1975 and U.S. Pat. No. 5,151,092 issued to Buell on Sep. 29, 1992, each of which is incorporated herein by reference. Similarly, the following U.S. Patents are incorporated herein by reference for the purpose of disclosing suitable attachment means for joining components of a sanitary napkin: U.S. Pat. No. 4,573,986 issued Mar. 4, 1986 to Minetola, et al.; U.S. Pat. No. 3,911,173 issued Oct. 7, 1975 to Sprague, Jr.; U.S. Pat. No. 4,785,996 issued Nov. 22, 1978 to Zieker, et al.; and U.S. Pat. No. 4,842,666 issued Jun. 27, 1989 to Werenicz.

As used herein, the "longitudinal" dimension, direction, or axis of the diaper 20 is aligned front to back with respect to the wearer as the disposable absorbent article is worn. The "lateral" or "transverse" dimension, direction, or axis of the diaper 20 is orthogonal the longitudinal direction and is sideways aligned as the diaper 20 is worn. The "Z-direction" is orthogonal to both the longitudinal and transverse directions, and is illustrated in FIG. 3.

The embodiment described herein is exemplary of a product suitable for a wearer weighing about 7.3 kilograms to about 12.2 kilograms (16 to 27 pounds) and having ischia bones spaced about 3.0 centimeters to about 7.6 centimeters (1.2 to 3.0 inches) apart. However, it will be understood that if the spacer 210 and the diaper 20 are intended for use with smaller or larger wearers, including adults, the spacer 210 and the diaper 20 can be scaled accordingly.

The spacer 210 is preferably inflatable from the first thickness T1 to the second, substantially greater thickness T2. By "substantially greater" it is meant that T2 is at least about 5 times, and preferably at least about 50 times as great as T1. The spacer 210 preferably has a second thickness T2 (FIG. 7) in the Z direction of at least 0.64 centimeters (0.25 inch). The thicknesses T1 and T2 are measured under a Z-direction, compressive loading of 175 kilograms per square meter (0.25 pound per square inch), where the compressive loading is applied over an area having a circular area of application, or footprint, of about 6.45 square centimeters (1.0 square inch). The thicknesses are measured in a location which does not include material 300 or packet 500. The thickness measurement can be made using a dial indicator such as an Ames Gauge available from the Ames Corporation of Waltham, Mass. Another suitable measurement means includes a VIR Electronic Thickness Tester, Model II, available from the Thwing Albert Instrument Company of Philadelphia, Pa.

Figure 2:
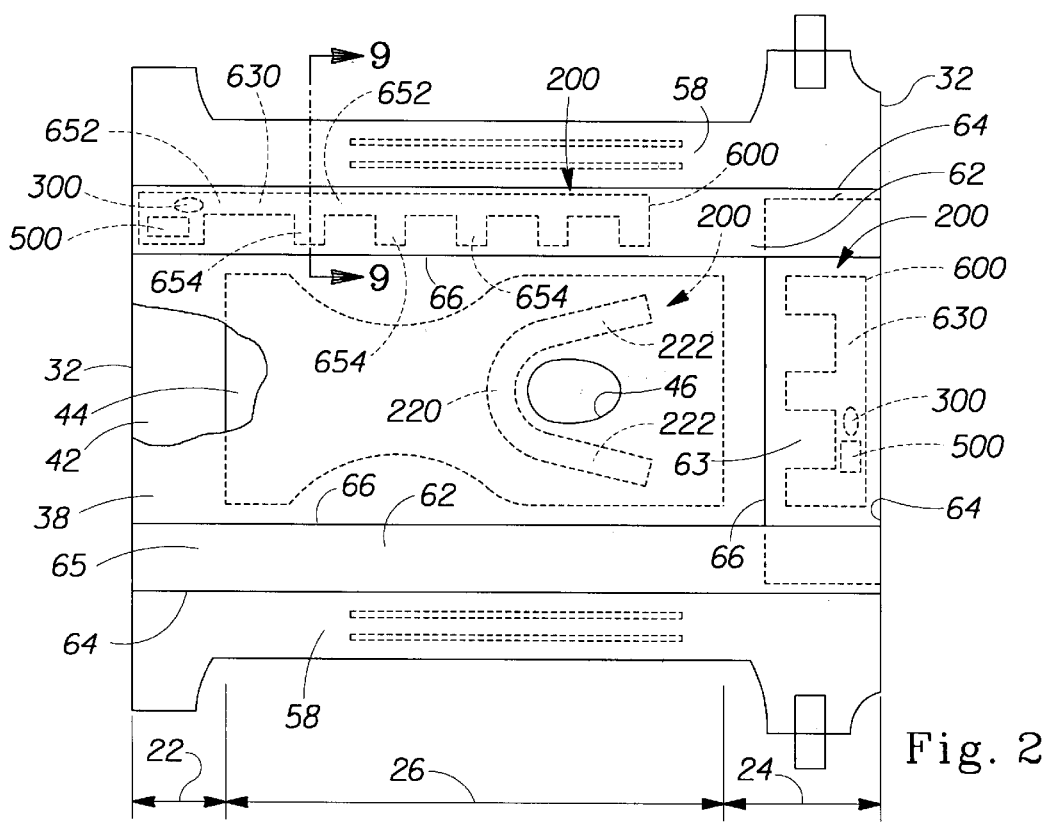
FIG. 2 is a top plan view of a disposable diaper embodiment of the present invention, the diaper shown partially cut-away and incorporating an inflatable U-shaped spacer and an inflatable barrier leg cuff component, the spacer and leg cuff component shown in phantom.
Figure 5:
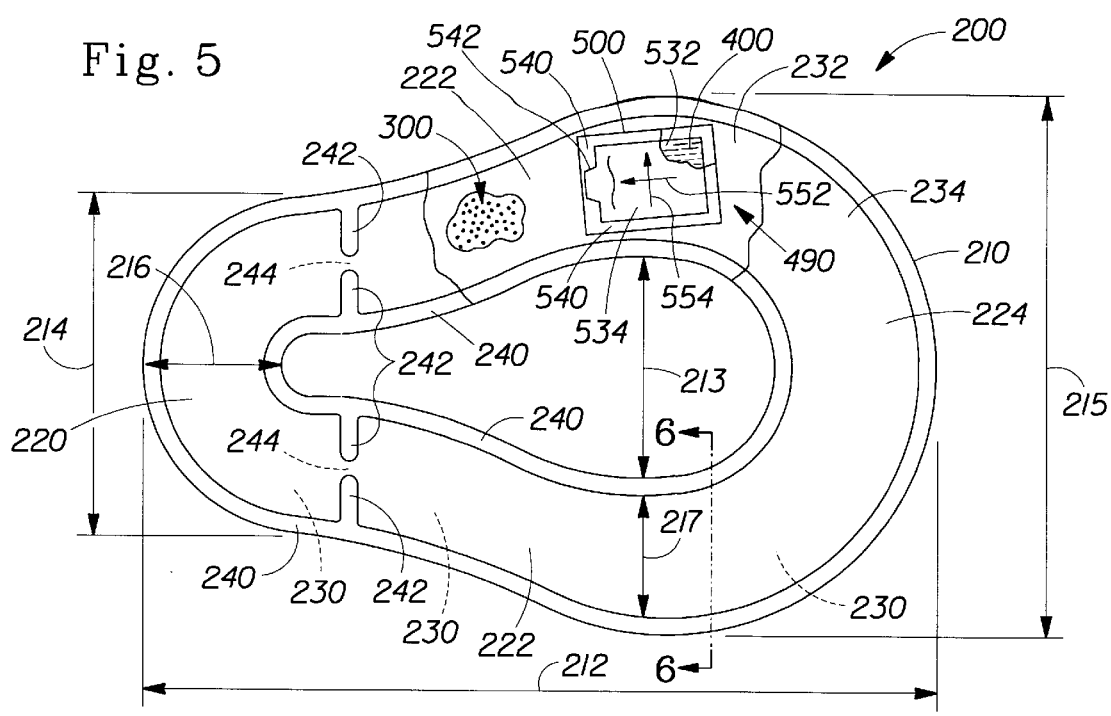
FIG. 5 is a top plan view of a keyhole shaped inflatable spacer shown partially cut-away to show a first gas evolving material and a second activating liquid enclosed in a breakable packet.

The spacer 210 illustrated in FIG. 1 and 5 has a generally "keyhole" shape comprising a closed figure. Alteratively, the spacer 210 can comprise a generally U-shaped figure opening rearward, as shown in FIG. 2, or any other suitable shape. In the alternatives shown in FIGS. 1 and 2, the spacer 210 includes a laterally extending portion 220 joining two longitudinally extending portions 222.

In one embodiment, the spacer 210 of FIG. 5 sized for the above mentioned wearers can have an overall longitudinal dimension 212 of about 8.9 to about 11.8 centimeters (3.5 to 4.6 inches) and a maximum transverse opening 213 of about 1.9 to 3.8 centimeters (0.75 inches to 1.5 inches). Such a spacer 210 may also have an overall transverse dimension 214 at the perimeter of the smaller end of the spacer 210 intended for disposition towards the front waist region 22 of about 5.1 centimeters (2.0 inches) and an overall transverse dimension 215 at the perimeter of the larger end of the spacer 210 intended to be oriented towards the rear waist region 22 of about 9.53 centimeters (3.75 inches). This spacer 210 may have an annular width 216 at the laterally extending portion 220 of about 1.2 centimeters (0.5 inches), and an annular width 217 at the longitudinally extending portions 222 of about 3.2 centimeters (1.2 inches).

The diaper 20 sized to fit the aforementioned range of wearers may be made having a topsheet 38 with a longitudinal dimension of about 43.8 centimeters (17.25 inches) and a backsheet 42 having a longitudinal dimension of about 46.4 centimeters (18.25 inches). The topsheet 38 and the backsheet 42 according to the present invention may have a transverse dimension, at the crotch region 35, of about 15.9 centimeters (6.25 inch) and about 21.3 centimeters (8.4 inches) respectively.

The difference in dimensions between the topsheet 38 and the backsheet 42 foreshortens the topsheet 38 relative to the backsheet 42 creating the void space 211 therebetween, even with the absorbent core 44 disposed intermediate the topsheet 38 and the backsheet 42. The topsheet 38 and upper layer 44U of the absorbent core 44 preferably comprise apertures 46 and 47 respectively. The apertures 46 and 47 are registered with one another to provide a passageway for the communication of fecal material from the wearer's anal opening into the void space 211.

As used herein, a "void space" is a cavity intermediate the topsheet 38 and the backsheet 42, which cavity is sized to accept fecal material. A void space 211 can be closed if the absorbent core 44 is compressed between the topsheet 38 and the backsheet 42 by the wearer's weight. When inflated to the have the second thickness T2, the spacer 210 can support the wearer's weight and thereby maintain the void space 211 such that the void space 211 has a thickness of at least about 0.65 centimeters (0.25 inch) and a volume of at least about 16.4 cubic centimeters (1.0 cubic inches).

Examining the components of the diaper 20 in more detail, the topsheet 38 and backsheet 42 are generally coextensive and at least partially peripherally joined together. As used herein the term "joined" refers to the condition where a first member or component is affixed or connected to a second member or component, either directly, or indirectly, where the first member or component is affixed or connected to an intermediate member or component which in turn is affixed or connected to the second member or component.

The topsheet 38 and backsheet 42 may be joined by any means well known in the art, such as adhesive bonding, ultrasonic bonding or heat sealing. A particularly preferred method of joining the topsheet 38 and backsheet 42 is using hot-melt adhesive such as manufactured by Century Adhesives, Inc. of Columbus, Ohio and marketed as Century 5227; HL1258 adhesive sold by the H. B. Fuller Company of St. Paul, Minn.; or Findley Adhesive H2031 available from the Findley Adhesive Company of Elmgrove, Wis. In a particularly preferred embodiment, adhesive joining is accomplished by longitudinally oriented adhesive bands or spirals.

As used herein, the term "absorbent core" refers to any component of the diaper 20 used for absorbing and retaining body exudates. The absorbent core 44 may have opposed major faces and may, if desired, be encased by one or more layers of tissue (not shown), or may be coated with a release agent to reduce friction against the fecal material.

The tissue layer, if present, improves the tensile strength of the absorbent core 44 and reduces its tendency to split or clump when wetted. The tissue layer may further improve transverse wicking of fluids and more evenly distribute absorbed liquids throughout the absorbent core 44.

A tissue layer having a basis weight of approximately 16 grams per square meter (10 pounds per 3,000 square feet) and an air permeability of approximately 30 cubic meters per minute per square meter (100 cubic feet per minute per square foot) and a differential pressure of 13 millimeters of water (0.5 inch of water) has been found to work well.

The absorbent core 44 may be made from a variety of commonly used natural or synthetic materials, including, but not limited to, comminuted wood pulp, typically referred to as airfelt. If desired, the absorbent core 44 may further contain particulate or fibrous absorbent gelling materials as is commonly used in the art. In particular, the absorbent core 44 may be made in accordance with the teachings of commonly assigned U.S. Pat. No. 4,610,678 issued Sep. 9, 1986 to Weisman et al.; U.S. Pat. No. 5,137,537 issued Aug. 11, 1992 to Herron et al.; U.S. Pat. No. 4,950,264 issued to Osborn Aug. 21, 1990; U.S. Pat. No. 4,834,735 issued to Alemany et al. May 30, 1989; U.S. Pat. No. 5,147,345 issued Sep. 15, 1992 to Young et al.; and European Patent Application No. 0 198 683 published Oct. 22, 1986 in the name of Duenk et al., which patents are incorporated herein by reference for the purpose of showing how to make an absorbent core 44 suitable for use with the present invention. Absorbent gelling materials made in accordance with commonly assigned U.S. Pat. No. Re. 32,649 issued Apr. 19, 1988 to Brandt et al. have been found suitable for use in a diaper 20 according to the present invention.

If desired, the lower layer 44L of the absorbent core 44 may have discrete storage and acquisition zones. The storage zone has a higher average density and higher average basis weight than the acquisition zone, so that the acquisition zone may effectively and efficiently acquire rapidly discharged liquids and transport the same to the storage zone for long term containment. Such a lower layer 44L may be made in accordance with above-referenced U.S. Pat. No. 4,834,735.

Figure 4:
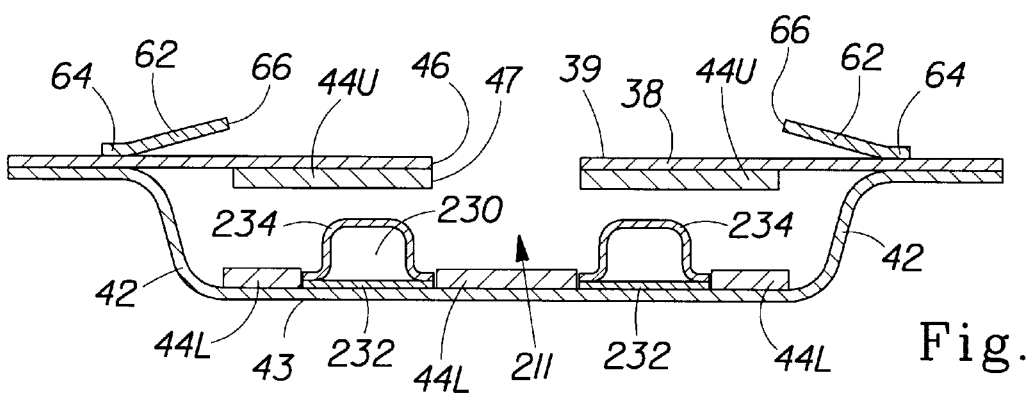
FIG. 4 is a cross-sectional view taken along line 3—3 of FIG. 1, with the spacer joined to the backsheet.

FIGS. 3 and 4 illustrate an upper layer 44U which is joined to the underside of the topsheet 38 and a lower layer 44L which is joined to the upper side of the backsheet 42. The absorbent core 44 has longitudinal and transverse dimensions generally less than, those of the topsheet 38 and the backsheet 42. The lower layer 44L of the absorbent core 44 may be made of a variety of sizes and shapes, such as rectangular or hourglass. Of course, a single layer absorbent core 44, as is well known in the art may be utilized.

The upper and lower layers 44U and 44L of the absorbent core 44 may be adhesively joined to the topsheet 38 and backsheet 42, respectively, or joined thereto by any attachment means well known in the art.

Particularly preferred attachment means are adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minn. and XPO-9-035 adhesive manufactured by the Minnesota Mining and Manufacturing Company of St. Paul, Minn.

Preferably, the lower layer 44L of the absorbent core 44 extends the entire longitudinal dimension of the diaper 20 between the front waist region 22 and the rear waist region 24, but does not intrude into either the front waist region 22 or the rear waist region 24. The upper layer 44U of the absorbent core 44 insulates the wearer from the impression and applied pressures of the spacer 210, which occur when the wearer is sitting while wearing the diaper 20. For this reason, the upper layer 44U of the absorbent core 44 should be present at least between the rear waist region 24 and the aperture 46.

Preferably, the exposed faces of the upper layer 44U and the lower layer 44L (those faces not attached to the topsheet 38 or the backsheet 24 respectively) are well defined and do not allow a significant quantity of loose fibers to intrude into the void space 211. Intrusion of a significant quantity of loose fibers into the void space 211 from the absorbent core 44 could interrupt (if not block) the transport of fecal material in the longitudinal direction, and prevent the isolation of such fecal material from the skin of the wearer.

Referring back to FIG. 1, the "topsheet" refers to any liquid pervious facing of the diaper 20 which contacts the skin of the wearer while the diaper 20 is worn and prevents substantial contact of the absorbent core 44 with the skin of the wearer. The topsheet 38 is preferably compliant, tactilely pleasant and non-irritating to the skin of the wearer. Preferably the topsheet 38 is treated to be hydrophilic, to more readily transport body exudates to the absorbent core 44.

A suitable topsheet 44 may be manufactured from materials such as porous foams, apertured plastic films, natural fibers (e.g., wood fibers or cotton fibers), synthetic fibers (e.g., polyester or polypropylene fibers) or a combination of the foregoing. A particularly preferred topsheet 38 comprises polypropylene fibers having a denier of about 2.2 and a length of about 15.9 millimeters (0.62 inches). The topsheet 38 may be manufactured according to a number of techniques. For example, the topsheet 38 may be a nonwoven web of fibers spunbonded, carded, wet-laid, meltblown, hydroentangled, combinations of the above, or the like.

A particularly preferred topsheet 38 is carded and thermally bonded and has a basis weight of about 18 to about 25 grams per square meter. A suitable topsheet 38 is marketed by Veratec, Inc., Division of International Paper Company of Walpole, Mass. under the designation P-8.

Alternatively, the topsheet 38 can comprise a formed film. The following patents are incorporate herein by reference for the purpose of describing suitable formed films: U.S. Pat. No. 3,929,135 issued to Thompson, Dec. 30, 1975; U.S. Pat. No. 4,324,246 issued to Mullane, et al., Apr. 13, 1982; U.S. Pat. No. 4,342,314 issued to Radel, et al., Aug. 3, 1982; U.S. Pat. No. 4,463,045 issued to Ahr, et al., Jul. 31, 1984; and U.S. Pat. No. 5,006,394 issued to Baird, Apr. 9, 1991. A suitable topsheet for the present invention is formed film described in one or more of the above patents and marketed on sanitary napkins by The Procter and Gamble Company of Cincinnati, Ohio as DRI-WEAVE. The following documents are incorporated by reference for the purpose of disclosing the use of surfactants for treating the topsheet to be hydrophilic: U.S. Statutory Invention Registration No. H1670, "Absorbent Article Having A Nonwoven and Apertured Film Coversheet" published Jul. 1, 1997 in the name of Aziz, et al.; and above referenced U.S. Pat. No. 4,950,254.

The topsheet 38 may include elastic elements or an elastic panel intermediate the lateral axis 34 and the rear waist region 24. Such an elastic panel maintains the topsheet 38 close to the wearer's skin, and helps to maintain registration of the aperture 46 with the anal opening. A suitable elastic panel may be incorporated according to the teachings of commonly assigned U.S. Pat. No. 5,032,120 issued Jul. 16, 1991 to Freeland et al., which patent is incorporated herein by reference for the purpose of showing how to make material suitable for the elastic panel and incorporate the elastic panel into the topsheet 38, and commonly assigned U.S. Pat. No. 5,037,416 issued Aug. 6, 1991 to Allen et al., which patent is incorporated herein by reference for the purpose of illustrating a particularly preferred material of construction for the elastic panel.

Referring to FIGS. 1–2, the aperture 46 is preferably laterally centered on the longitudinal axis 36. The aperture 46 may be of any shape desired with a suitable shape being an oval having a longitudinal dimension of about 5.1 centimeters (2.0 inches) and a transverse dimension of about 3.8 centimeters (1.5 inches). The rearwardmost edge of the aperture 46 is disposed at least about 12.7 centimeters (5.0 inches), and preferably about 15.2 centimeters (6.0 inches) to about 21.6 centimeters (8.5 inches) from the rear edge 32 of the diaper 20 while it is worn. Alternatively, the aperture 46 may be a slit which is generally closed prior to or during use and which opens to let fecal matter pass through.

It is desirable that the spacer 210 be registered with the apertures 46 and 47. A spacer 210 registered with the apertures 46 and 47 spaces a part of the diaper 20 underlying the apertures 46 and 47, such as a part of the absorbent core 44 or backsheet 42, away from the wearer's body. Body exudates, such as solid and liquid fecal matter, can thereby pass through the apertures 46 and 47 and into void space 211.

Referring to FIGS. 3–4, aperture 47 is aligned with the aperture 46, and preferably has a shape the same as, or similar to, the shape of aperture 46. Preferably, the spacer 210 is registered with the apertures 46 and 47, such that spacer 210 does not substantially obstruct aperture 46 or aperture 47, and such that at least a portion of each aperture 46 and 47 is disposed intermediate the longitudinally extending portions 222 of spacer 210.

The backsheet 42 is preferably impervious to fluids, such as urine, and prevents fluids absorbed by and contained in the absorbent core 44 from wetting undergarments, clothing and bedding. As used herein the "backsheet" refers to any barrier disposed outwardly of the absorbent core 44 as the diaper 20 is worn and which contains absorbed liquids within the diaper 20. The backsheet 42 is preferably manufactured from a thin plastic film, although other flexible liquid impervious materials may also be used. As used herein, the term "flexible" refers to materials which are compliant and will readily conform to the general shape and contours of the human body.

The backsheet 42 may be a polyolefinic film, such as polyethylene, having a thickness of about 0.01 millimeters to about 0.051 millimeters (0.0005 to 0.002 inches). If desired, the backsheet 42 may be embossed or matte finished to provide a cloth-like appearance and may be breathable. A suitable backsheet 42 can be made from a blend of about 45 to 90 percent linear low density polyethylene and about 10 to 55 percent polypropylene. Suitable backsheet films are sold by Tredegar Industries, Inc. of Terre Haute, Ind. under the designation RR8220 blend for blown films and RR5475 blend for cast films; by Clopay Corp. of Cincinnati, Ohio under the designation P18-0401; and by Ethyl Corp., Visqueen Division, of Terre Haute, Ind. under the designation XP-39385.

Other suitable backsheet materials can include breathable materials that permit vapors to escape from diaper 20 while still preventing exudates from passing through backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable materials are described in greater detail in PCT Application No. WO 95/16746, published on Jun. 22, 1995 in the name of E. I. DuPont, U.S. Pat. No. 5,865,823, issued on Feb. 2, 1999 in the name of Curro, and U.S. Pat. No. 5,571,096 issued to Dobrin et al. on Nov. 5, 1996. Each of these references is hereby incorporated by reference herein.

Referring again to FIGS. 1 and 5, the spacer 210 can have a keyhole shape comprising a generally closed figure. The closed figure shape shown in FIGS. 1 and 5 provides the spacer 210 longitudinally disposed so that the end having the smaller lateral width 214 is oriented towards the front waist region 22 and the end having the greater transverse width 215 is oriented towards the rear waist margin 24. This keyhole shape shown in FIGS. 1 and 5 comfortably accommodates the thighs of the wearer, due to the smaller lateral width 214.

The laterally extending portion 220 of spacer 210 is preferably disposed intermediate the front waist region 22 and the aperture 46, and extends between longitudinally extending portions 222. A laterally extending portion 224 is positioned intermediate the rear waist region 24 and the aperture 46. Other spacer shapes comprising a generally closed figure can include, but are not limited to, circles, ovals, and polygons.

Alternatively, the spacer 210 can have a shape comprising an open figure, such as shown in FIG. 2. A laterally extending portion 220 can connect longitudinally extending portions 222 to form a generally U-shaped configuration that opens rearwardly. Where the laterally extending spacer portion 220 is omitted, the spacer 210 in FIG. 2 can comprise two separate longitudinally extending portions 222 registered with the aperture 46.

Figure 6:
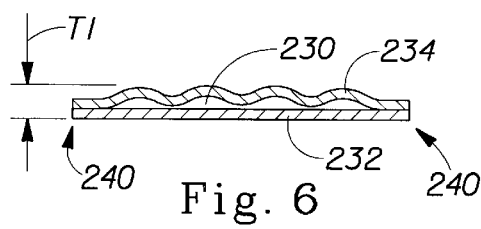
FIG. 6 is a cross-sectional view taken along line 6—6 of FIG. 5 showing the spacer having a first uninflated thickness.
Figure 7:
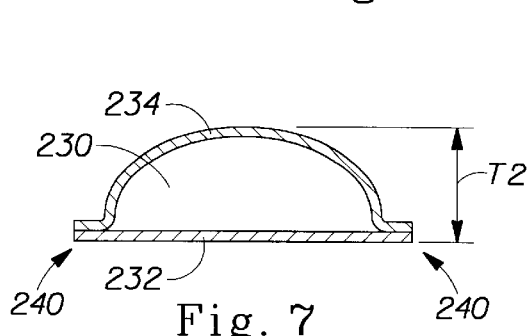
FIG. 7 is a cross-sectional view taken along line 6—6 of FIG. 5 showing the spacer having a second inflated thickness, wherein one of the spacer chamber walls is substantially more extensible than the other or is preformed.

Referring to FIGS. 5–7, a spacer 210 according to the present invention comprises one or more inflatable chambers 230. Inflatable chambers 230 can be formed by peripherally joining two chamber walls 232 and 234 at seams 240. A portion of chamber wall 234 is cut away in FIG. 5 to show the first material 300 and the breakable packet 500 containing the second activating material 400, all disposed in an inflatable chamber 230. The breakable packet 500 can be broken by the wearer or diaperer applying pressure to the packet 500 at any desired time at the point of use of the diaper 20.

Seams 240 can include seam extensions 242 for separating adjacent inflatable chambers 230, as shown in FIG. 5. Seam extensions 242 preferably extend laterally to provide one or more laterally extending hinge lines. Such hinge lines reduce the longitudinal stiffness of the spacer 210 when the chambers 230 are inflated. Adjacent seam extensions 242 can be spaced apart to provide a channel 244 interconnecting adjacent chambers 230. Channels 244 permit gas generated in one chamber 230 to inflate interconnected adjacent chambers 230 so that first and second materials 300 and 400 need not be located in each chamber 230.

Alternatively, the chamber walls 232 and 234 can be vacuum formed to provide such hinge lines.

The first and second materials 300 and 400 should be non-toxic and combine to evolve an inert gas which is non-toxic in the quantities generated. The first gas evolving material 300 is preferably a combination of a bicarbonate, such as sodium bicarbonate or potassium bicarbonate, with a powdered acid to provide carbon dioxide when wetted by the second activating material 400. Suitable powdered acids include, but are not limited to citric acid, tartaric acid, terephthalic acid, and salicylic acid. A suitable first material 300 comprises an effervescent powder containing heat treated sodium bicarbonate, citric acid, and salicylic acid and is available in tablet form from Miles, Inc. of Elkhart, Ind. under the trade name ALKA-SELTZER.

The first material 300 is preferably soluble in the second activating material. The preferred second activating material 400 comprises water.

In an alternative embodiment, the first material 300 can comprise a bicarbonate and the second activating material 400 can comprise one of the above listed powdered acids dissolved in water.

The speed of inflation of the chamber 230 can be controlled by forming the first material 300 as a fine powder (rapid inflation), or as a compressed tablet (slow inflation). In addition, the first material 300 can have a coating that dissolves in the second material 400 to provide a time delayed inflation.

Of course, the amounts of first and second materials 300 and 400 will vary depending upon the inflated volume of the chambers 230. The amounts of the bicarbonate and the powdered acid which are mixed to evolve a given volume of carbon dioxide when dissolved in water can be determined by stoichiometry. Commonly assigned U.S. Pat. No. 3,881,491 issued to Whyte on May 6, 1975 is incorporated herein by reference for the purpose of showing a method for calculating the amounts of a bicarbonate and a powdered acid which can be mixed to provide a given volume of carbon dioxide gas when dissolved in water.

The breakable packet 500 should contain at least enough water or other activating second material 400 to dissolve the quantity of the first material 300 disposed in the chamber. The amount of water required will depend upon the solubility and quantity of the components of first material 300. In general, for the bicarbonates and powdered acids listed above, the packet 500 may contain between at least about two milliliters of water per gram of first material 300 to about eight milliliters of water per gram of first material 300.

Figures 5A, 5B:
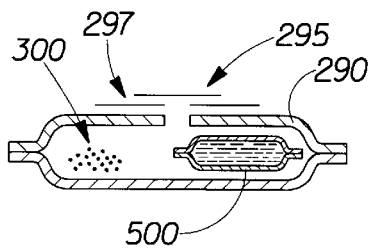
FIG. 5A is a cross-sectional view of a gas permeable envelope containing both the gas evolving material and the packet containing the activating material.
FIG. 5B is a cross-sectional view of an alternative embodiment of the present invention shown in FIG. 5A.

The first material 300 can be unconstrained in the inflatable chamber 230, or adhesively adhered to one the walls 232 and 234 to prevent the first material 300 from shifting during shipping and storage such that it is not adjacent breakable packet 500. More preferably, the material 300 and the breakable packet 500 can be enclosed in an envelope 290 comprising a gas permeable material, as shown in FIG. 5A. The gas permeable envelope 290 is disposed in the chamber 230 and comprises a material such as a woven, nonwoven, or apertured film which is permeable to the gas evolved when the first material 300 is combined with the second material 400. The gas permeable envelope 290 can be adhered to one of the walls 232, 234. By the phrase "gas permeable material" it is meant that at least 500 cubic centimeters, preferably at least 5000 cubic centimeters, and more preferably at least 50,000 cubic centimeters of the evolved gas at standard temperature and pressure can pass through such a material having a surface area of 6.45 square centimeters (1.0 square inch) in one hour when the pressure difference across the material is 0.068 atmosphere (1.0 psi) during the one hour interval.

The envelope 290 may be hydrophobic, or at least treated to be hydrophobic. The term "hydrophobic" can be defined in terms of the contact angle between a liquid and a surface. The American Chemical Society Publication "Contact Angle, Wettability, and Adhesion," edited by Robert F. Gould and copyrighted in 1964 is incorporated herein by reference for the purpose of showing how the contact angle can be determined. A surface is hydrophobic for the purpose of this invention if the contact angle is greater than about 80 degrees, and preferably at least 90 degrees. A suitable material from which the envelope 290 can be formed is a spunbond hydrophobic polypropylene nonwoven having a fiber denier between 2.5 and 3.0 and a basis weight between about 16 grams per square meter and about 30 grams per square meter such as is marketed by Fiberweb—North America of Simpsonville, S.C.

More preferably, the envelope 290 comprises a gas permeable, liquid impermeable material or element so as to prevent any of the second activating material (e.g., water) from escaping into the inflatable chamber 230. This ensures that the second material is all available to the first material for the gas-evolving reaction. It also ensures that the second material does not escape into other parts of the diaper or onto the wearer's skin. Suitable gas permeable, liquid impermeable materials for the envelope 290 include films available as 201-1999 and BR106 from Clopay Corp. of Cincinnati, Ohio. Other suitable materials include the breathable materials described herein with respect to the backsheet.

Another advantage of the present invention is that the rate of inflation of the inflatable chamber 230 may be controlled by varying the gas diffusion rate of the gas-permeable, liquid impermeable material. For example, decreasing the gas diffusion rate of the envelope 290 will generally result in a decreased inflation rate of the chamber 230 and increasing the gas diffusion rate of the envelope 290 will generally result in an increased inflation rate of the chamber 230. Slower inflation rates may be desirable to allow time to apply clothing over the article before full inflation of the chamber 230 or to provide for unobtrusive creation of the inflatable component.

In one preferred embodiment, as shown in FIG. 5B, the envelope 290 comprises a gas impermeable material comprising an expansion control mechanism. As shown, the expansion control mechanism may include an inflation control mechanism such as gas release mechanism 295 which helps to control passage (i.e., allow flow only at certain pressures or at certain rates) of the evolved gas from the envelope 290 into the inflatable chamber 230. The gas release mechanism 295 may comprise a valve 297 or any other suitable device for regulating the flow of gas. A suitable valve is available as a Pli-Valv® Pressure Relief Valve from Plitek®, L.L.C. of Des Plaines, Ill. In this embodiment, the walls 232 and 234 of the envelope 290 are preferably substantially gas impermeable, and are preferably made from a material which is soft, flexible, and, preferably, thermoformable. (As used herein, the term "substantially gas impermeable" means materials having an MVTR of less than about 20 $g/m^2$ per 24 hours. Preferably, the substantially gas impermeable materials of the present invention have an MVTR of less than about 10 $g/m^2$ per 24 hours.)

The MVTR of a sample is measured as follows: a known amount of $CaCl_2$ is put into a flanged cup. A sample material is placed on top of the cup and held securely by a retaining ring and gasket. The assembly is then weighed and recorded as the initial weight. The assembly is placed in a constant temperature (40.degree. C.) and humidity (75% RH) chamber for five (5) hours. The assembly is then removed from the chamber and allowed to equilibrate for at least 30 minutes at the temperature of the room where the balance is located. The assembly is then weighed and recorded as the final weight. The mass vapor transmission rate (MVTR) is calculated and expressed in g/m.sup.2/24 hr. using the following formula:

$$MVTR = \frac{(\text{final weight} - \text{initial weight}) \times 24.0}{\text{area of sample in meters} \times 5.0 \text{ (time in chamber)}}$$

Suitable materials from which the walls 232 and 234 can be made include films, metallic foils and other substantially gas impermeable materials and laminates thereof. For instance, a suitable film is a polyethylene film having a thickness of from about 0.005 mm to about 0.051 mm manufactured by Clopay Corp. of Cincinnati, Ohio under the designation P-18-1401, and by Tredegar Industries of Terre Haute, Ind. under the designations X8297 and HTS-5, FSII. Other suitable materials from which the walls 232 and 234 can be formed include RR8220 blown films and RR5475 cast films manufactured by Tredegar Industries. Another suitable material from which one or both of the walls 232 and 234 can be made is a polyethylene film available from Tredegar Industries designated C-8323. Still other suitable materials from which the walls 232 and 234 may be formed include a 3.0 mil nylon/LDPE/Surlyn coextruded film available as C735H-014 from Printpack, Inc., of Atlanta, Ga., and 3.0 mil nylon/LLDPE coextruded films available as C733H-010 and C733-010, also available from Printpack, Inc. These materials and other types of valves may also be employed to control gas flow in other embodiments, such as those described herein, wherein the envelope 290 comprises a gas permeable, liquid impermeable material. In such embodiments, the other types of valves may function as a pressure release mechanism to prevent the envelope 290 from bursting when expanded.

In certain embodiments, the gas evolving material may be disposed within an envelope comprising a water soluble film. In such embodiments, the gas evolving material is held within or behind the water soluble material. The water in the activating material acts to dissolve at least a part of the water soluble material prior to activating the gas-evolving reaction. This delays the inflation of the expandable element. Thus, the time required for the chamber 230 to reach 90% of its ultimate thickness may be predetermined and is preferably in the range of about 10 to about 20 minutes. Suitable water soluble films include PVA films supplied by Chris-Craft Industrial Products, Inc. of South Holland, Ill. under the trade designations MONOSOL M7031, M7030, M8630, M8534, or E6030 film; or from H. B. Fuller Company of St. Paul, Minn. as HL 1636 or HL 1669-X.

The inflatable chambers 230 should preferably maintain an inflated thickness T2 of at least 0.635 centimeters (0.25 inch) for at least one hour, preferably at least three hours, and more preferably at least six hours when the spacer 210 is subjected to a Z-direction compressive load of 175 kg per square meter (0.25 pounds per square inch), and should not completely flatten or rupture when subjected to an impact load such as can result when the wearer sits, or suddenly falls down.

Such a material has machine direction tensile strength at rupture of between 790 to 1600 grams/centimeter (2000 to 4000 grams/inch), a machine direction tensile elongation at rupture of between about 400 to 700 percent, a cross machine direction tensile strength at rupture of between 390 and 1200 grams/centimeter (1000 and 3000 grams/inch), and a cross machine direction elongation at rupture of between 400 and 800 percent.

The tensile strengths and elongations listed above are measured using a constant rate of elongation tensile testing machine, such as an Instron Model 1122 made by the Instron Corp. of Canton, Ohio, operated at an elongation rate of 0.85 cm/sec (20 in/min) with a 2.54 cm (1 inch) sample width and a 5.08 cm (2 inch) gauge length. Another suitable material from which walls 232, 234 may be formed comprises an elastomeric film such as a film designated Exx-7 available from the Exxon Corporation of Houston, Tex.

Figure 8:
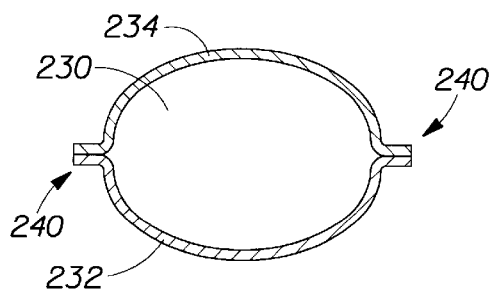
FIG. 8 is a cross-sectional view taken along line 6—6 of FIG. 5, showing the spacer having a second inflated thickness, wherein both spacer chamber walls deform upon inflation to form a generally oval shaped inflated spacer cross-section.

One or both of the walls 232 and 234 can be pre-formed, such as by thermoforming, vacuum forming or embossing. Referring to FIG. 7, wall 234 can be vacuum formed to provide a generally semi-circular cross-section upon inflation of chamber 230. Referring to FIG. 8, walls 232 and 234 can be joined without performing, such that both walls 232 and 234 comprise generally flat films which deform to provide a generally oval cross-section upon inflation of chamber 230.

The walls 232 and 234 can be joined to form seams 240 by any suitable joining method such as heat/pressure sealing, adhesive bonding, ultrasonic bonding, or the like. Suitable seams 240 can be formed using a Vertrod Thermal Impulse Heat Sealer Model 15MGC marketed by the Vertrod Corporation of Brooklyn, N.Y.

Referring to FIGS. 3 and 4, the spacer 210 can be joined to the diaper 20 by joining one of the walls, such as wall 232, to an underlying structure, such as the topsheet 38, backsheet 42, or absorbent core 44.

The spacer 210 can be joined to the underlying structure by any suitable joining method such as heat/pressure sealing, adhesive bonding, ultrasonic bonding, or the like. Suitable adhesives include the Century 5227 adhesive and the Findley Adhesive H2031 listed above.

In FIG. 3, spacer 210 is joined to upper core layer 44U. Alternatively, in embodiments not having an upper core layer 44U, the spacer 210 can be joined directly to the topsheet 38 or the absorbent core 44. In FIG. 4 the lower core layer 44L is formed around the spacer 210 and the spacer 210 is joined to backsheet 42. In an alternative to the embodiment shown in FIG. 4, chamber wall 232 can comprise a portion of backsheet 42, and wall 234 is joined directly to the backsheet at the seams 240.

Referring to FIG. 5, the breakable packet 500 can be formed by peripherally joining two flexible walls 532 and 534 along seams 540. A portion of the wall 534 is cut away in FIG. 5 to show the second material 400 contained in the packet 500. The two walls 532 and 534 can be formed from a liquid impervious plastic film such as a polyethylene, polypropylene, or polyester film. A particularly suitable film comprising a foil layer and a sealant layer is available as E-13056-99 from American National Can Co. of Chicago, Ill. The two walls 532 and 534 can be generally rectangular, and can be peripherally joined along 3 sides to form a pocket. The pocket can be partially filled with the second activating material 400 (e.g., water). The fourth side of the walls 532 and 534 can then be sealed along a seam 540 to close the pocket and contain the water. The pocket so formed is preferably only partially filled such as to about 80 to 90 percent capacity to prevent the breakable packet 500 from inadvertently rupturing during packaging or shipping.

The two walls 532 and 534 can be joined at seams 540 by any suitable method such as by heat/pressure sealing, adhesive bonding, ultrasonic bonding, or the like. Suitable seams 540 can be formed using the Vertrod Model 15MGC heat sealer listed above.

The wearer or diaperer may expand the spacer 210 by combining the first and second materials such as by squeezing the portions of the diaper 20 overlying and underlying the packet 500 between the thumb and forefinger or otherwise rupturing the packet 500. The packet 500 can be located such that it can be squeezed and broken before or after the diaper 20 is fastened to the wearer. The envelope 290 holding the packet 500 can be joined to chamber wall 232 (or to the backsheet 42 if chamber wall 232 comprises a portion of backsheet 42) such that the packet can be easily accessed for squeezing between portions of the backsheet 42 either before or after the diaper 20 is fastened on the wearer.

In an alternative embodiment the packet 500 can be disposed in one of the front and rear waist regions 22, 24 so that it can be easily accessed before or after the diaper 20 is fastened to the wearer. For instance, the packet 500 and first material 300 can be disposed in a chamber in one of the front and rear waist regions 22, 24. The chamber containing the packet 500 and first material 300 can be fluidly connected to an inflatable chamber 230 by a slender tube. The chamber in the waist region 22, 24 and the slender tube can be formed by extensions of flexible chamber walls 232, 234.

The breakable packet 500 can be weakened to break along a predetermined direction so that the second activating material 400 is directed toward the first material 300. Referring to FIG. 5, the packet 500 can include a nozzle 542 formed by reducing the width of a seam 540 adjacent the first material 300. The nozzle 542 directs the activating material 400 in the packet 500 toward the first material 300. Alternatively, the packet walls 532 and 534 can be formed from a material having a different tensile elongation at rupture along two mutually perpendicular directions.

The direction 552 is parallel to the machine direction of the material from which walls 532 and 534 are formed, and the direction 554 is parallel to the cross machine direction of the material from which walls 532 and 534 are formed. The machine direction tensile elongation at rupture is preferably significantly lower than (e.g., less than half) the cross machine direction elongation at rupture, so that the walls 532 and 534 rupture along a tear line parallel to the cross machine direction (direction 554). The opening so formed can direct at least some of the second material 400 toward the first material 300.

A suitable material for forming packet walls 532 and 534 and having a machine direction tensile elongation at rupture which is between about ⅓ and ½ the cross machine direction tensile elongation at rupture is available from Tredegar Industries of Terre Haute, Ind. under the designation C-8570 and having a thickness of about 0.028 mm (1.1 mil). Such a material has machine direction tensile strength at rupture of between 590 and 1400 grams/centimeter (1500 to 3500 grams/inch), a machine direction elongation at rupture of between about 100 to 300 percent, a cross machine direction tensile strength at rupture of between 400 and 790 grams/centimeter (1000 and 2000 grams/inch), and a cross machine direction elongation at rupture of between 300 and 700 percent.

The tensile strengths and elongations listed above are measured using a constant rate of elongation tensile testing machine, such as an Instron Model 1122 made by the Instron Corp. of Canton, Ohio, operated at an elongation rate of 0.85 cm/sec (20 in/min) with a 2.54 cm (1 inch) sample width and a 5.08 cm (2 inch) gauge length.

By way of an example, an inflatable spacer 210 having the above mentioned dimensions and formed from the above mentioned Tredegar C-8323 film can be inflated to a thickness T2 of about 1.27 centimeters (0.5 inch) with about 300 mg of ALKA-SELTZER and about 4.0 ml of water in packet 500. However, alternative embodiments are contemplated including different amounts of the first and second materials. For example, embodiments including 5 grams of water and 1 gram of ALKA-SELTZER have been found to work well.

Figure 9:
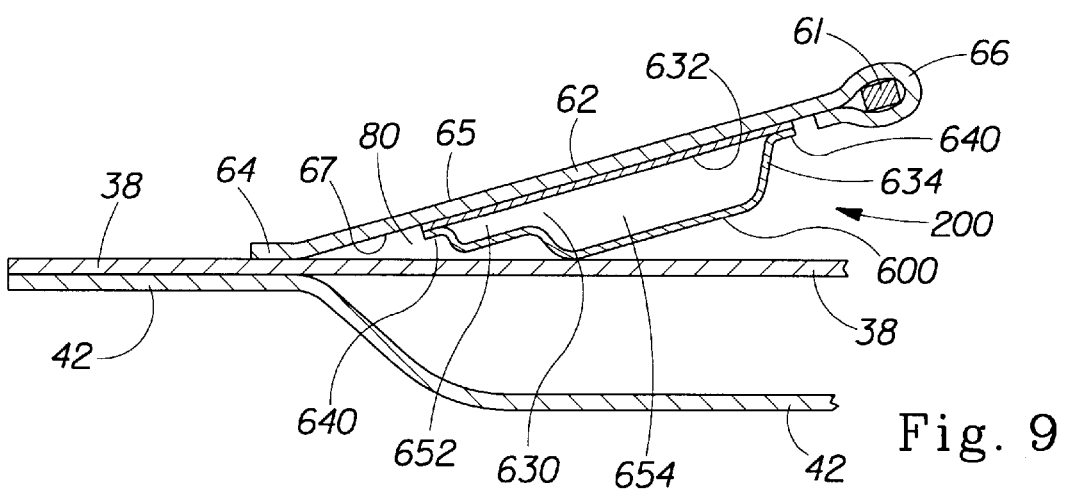
FIG. 9 is a cross-sectional view taken along line 9—9 of FIG. 2 showing an inflated component, comprising a portion of a barrier leg cuff.

Referring to FIGS. 2 and 9, the diaper 20 can include an expandable component 200 comprising a seal member 600 (shown in phantom in FIG. 2). The seal member 600 comprises a portion of a seal means for reducing leakage of body exudates from between the diaper 20 and the wearer's skin. Such a seal means can comprise a barrier leg cuff 62 for reducing leakage from between the diaper 20 and the wearer's legs in the crotch region 26. Such a seal means can also comprise a barrier waist cuff 63 for reducing leakage from one of the front and rear waist regions 22, 24.

Above referenced U.S. Pat. No. 4,938,755 is incorporated herein by reference for the purpose of showing a suitable construction for the barrier cuffs 62 and 63. The seal member 600 will be described as it comprises a portion of a barrier leg cuff 62, it being understood that the following description can be easily adapted to provide a seal member 600 comprising a portion of a barrier waist cuff 63 shown in phantom in FIG. 2.

The barrier leg cuff 62 has a proximal edge 64 joined to a side flap 58 in the crotch region 26 and a longitudinally extending distal edge 66 which is not attached to an underlying diaper structure in the crotch region 26. The barrier leg cuff 62 may include an elastic spacing element 61 operatively associated with the distal edge 66 for spacing the distal edge 66 apart from the topsheet 38.

Referring to FIG. 9, the barrier leg cuff 62 has oppositely facing outward and inward surfaces 65, 67 extending between the proximal and distal edges 64, 66. The inward surface 67 faces an underlying diaper structure, such as topsheet 38. The seal member 600 is joined to the inward face 67 and is expandable to space the distal edge 66 apart from the topsheet 38. A channel 80 for receiving and holding body exudates is thereby formed between the barrier leg cuff 62 and the topsheet 38. The barrier leg cuff 62 shown in FIG. 9 comprises both the seal member 600 and an elastic spacing element 61. Alternatively, the elastic spacing element 61 can be omitted.

The seal member 600 is preferably inflatable and comprises at least one inflatable chamber 630 disposed intermediate the proximal and distal edges 64, 66. The inflatable chamber 630 can be formed between chamber walls 632 and 634 peripherally joined together at seams 640. Suitable materials for forming chamber walls 632 and 634 include those materials listed above for forming chamber walls 232 and 234. Seams 640 can be formed similarly to seams 240 described above. Chamber wall 632 can be joined to the inward surface 67 of the barrier leg cuff 62 by any suitable method such as heat/pressure bonding, adhesive bonding, or ultrasonic bonding, to secure the expandable component 600 to the barrier leg cuff 62.

The inflatable chamber 630 can comprise a generally longitudinally extending portion 652 and at least one generally laterally extending portion 654. The generally longitudinally extending portion 652 can be generally parallel to and juxtaposed with the proximal edge 64 of the barrier leg cuff 62. Referring to FIG. 2, the longitudinally extending portion 652 preferably extends into at least one of the front and rear waist regions 22, 24.

The first material 300 and the breakable packet 500 containing the second activating material 400 can be enclosed in an envelope 290 (FIG. 5A) comprising a gas permeable material; a gas permeable, liquid impermeable material; or a gas impermeable material comprising a gas release mechanism as described above, disposed within the longitudinally extending portion 652 and positioned in one of the front and rear waist regions 22, 24. The breakable packet 500 is positioned in the front waist region 22 in FIG. 2. Positioning the breakable packet 500 in one of the front and rear waist regions 22, 24 permits the wearer or diaperer to easily access and rupture the breakable packet 500 before or after the diaper 20 is fastened to the wearer.

The laterally extending portions 654 can extend intermediate the longitudinally extending portion 652 and the distal edge 66 of the barrier cuff 62. The laterally extending portions 654 can be interconnected by the longitudinally extending portion 652 such that portions 652 and 654 can be inflated by breaking a single packet 500. The chamber wall 634 can be preformed, such as by embossing or vacuum forming the chamber wall 634, such that the inflated thickness of portion 652 of inflatable chamber 630 is smaller than the inflated thickness of portions 654 of inflatable chamber 630.

Inflation of the laterally extending portions 654 causes chamber wall 634 to abut topsheet 38, and thereby bias the distal edge 66 apart from the topsheet 38. Because the inflated thickness of the longitudinally extending portion 652 is smaller than the inflated thickness of the laterally extending portions 654, body exudates can flow between adjacent laterally extending portions 654 and be held in the longitudinally extending channel 80 formed between the barrier leg-cuff 62 and the topsheet 38.

In the embodiments described above, the expandable component 200 is inflatable, and the first material 300 evolves gas upon combination with the second activating material 400. In an alternative embodiment, the first material 300 can comprise a material that swells or expands upon combining with, or being wetted by, the second activating material 400.

For example, first material 300 can comprise a number of absorbent materials, including but not limited to absorbent foams, absorbent gelling materials, or superabsorbent polymers which swell or expand upon being wetted. A suitable superabsorbent material for use as the first material 300 is disclosed in U.S. Pat. No. 4,610,678 issued Sep. 9, 1986 to Weisman, et al.

The diaper 20 is applied to the wearer by positioning the back waist region 24 under the wearer's back and drawing the remainder of the diaper 20 between the wearer's legs so that the front waist region 22 is positioned across the front of the wearer. The ends of the tape tab fasteners 54 are then secured, preferably to outward facing areas of the diaper 20.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An absorbent article comprising:
   a backsheet;
   a topsheet joined to at least a portion of the backsheet;
   an absorbent core intermediate the topsheet and the backsheet;
   an expandable component disposed in the absorbent article, the expandable component expandable from a first thickness to a second thickness; and
   a system for controlling the expansion of the expandable component from the first thickness to the second thickness, the system including:
      a predetermined amount of a first material disposed on the article; and
      a predetermined amount of a second material disposed on the article, wherein the second material is separated from the first material by a breakable barrier, and wherein the first and second materials are combinable by breaking the barrier to expand the expandable component; and
      an expansion control mechanism which is capable of controlling the rate of expansion of the expandable component.

2. The absorbent article of claim 1 wherein at least one of the first or second materials evolves a gas upon combining of the first and second materials.

3. The absorbent article of claim 2 wherein the expansion control mechanism includes a gas permeable envelope and the first and second materials are contained in the gas permeable envelope.

4. The absorbent article of claim 3 wherein the gas permeable envelope is liquid impermeable.

5. The absorbent article of claim 1 wherein the expandable component comprises a spacer disposed between the topsheet and backsheet for maintaining a z-direction void space.

6. An absorbent article comprising:
   a backsheet;
   a topsheet joined to at least a portion of the backsheet;
   an absorbent core intermediate the topsheet and the backsheet;
   an inflatable component disposed in the absorbent article, the inflatable component inflatable from a first thickness to a second thickness, the inflatable component including at least one inflatable chamber;
   a gas evolving material disposed in fluid communication with the inflatable component, the gas evolving material producing a gas for inflation of the inflatable component upon combining with an activating material;
   a packet containing the activating material, the packet disposed such that opening the packet will permit exposure of the activating material to the gas evolving material, thereby inflating the inflatable component from the first thickness to the second thickness; and
   an inflation control mechanism which is capable of controlling the rate of inflation of the inflatable component.

7. The absorbent article of claim 6 wherein the inflation control mechanism includes a gas permeable envelope and the gas evolving material and activating material are contained in the gas permeable envelope.

8. The absorbent article of claim 7 wherein the gas permeable envelope is liquid impermeable.

9. The absorbent article of claim 7 wherein the gas permeable envelope is disposed within the inflatable component.

10. The absorbent article of claim 6 wherein the inflatable component comprises a spacer disposed between the topsheet and backsheet for maintaining a z-direction void space.

* * * * *